(12) United States Patent
Anderson

(10) Patent No.: US 6,600,951 B1
(45) Date of Patent: *Jul. 29, 2003

(54) TARGETING OF SEBACEOUS FOLLICLES AS A TREATMENT OF SEBACEOUS GLAND DISORDERS

(75) Inventor: Richard Rox Anderson, Lexington, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/464,137

(22) Filed: Dec. 16, 1999

Related U.S. Application Data

(63) Continuation-in-part of application No. 09/225,026, filed on Jan. 4, 1999, now Pat. No. 6,183,773.

(51) Int. Cl.⁷ .................................................. A61N 1/30
(52) U.S. Cl. .................. 604/20; 604/501; 604/289; 606/9
(58) Field of Search ............................. 604/500, 501, 604/289, 290, 20; 606/1, 9, 2, 10–13, 131, 133, 32, 33, 36; 424/401, 450, 70.8, 70.1; 514/859; 607/88, 89, 94, 108, 109

(56) References Cited

U.S. PATENT DOCUMENTS

| | | |
|---|---|---|
| 4,287,554 A | 9/1981 | Wolff |
| 4,651,739 A | 3/1987 | Oseroff et al. .............. 128/395 |
| 4,930,504 A | 6/1990 | Diamantopoulos et al. |
| 4,945,908 A | 8/1990 | Schneider |
| 5,019,034 A * | 5/1991 | Weaver et al. ................ 604/20 |
| 5,131,403 A * | 7/1992 | Haynes ....................... 128/760 |
| 5,226,907 A | 7/1993 | Tankovich ................... 606/133 |
| 5,234,940 A | 8/1993 | Kennedy et al. |
| 5,304,170 A | 4/1994 | Green .......................... 606/9 |

(List continued on next page.)

FOREIGN PATENT DOCUMENTS

| | | | |
|---|---|---|---|
| EP | 0 726 083 | 8/1996 | |
| WO | WO 94/06424 | 3/1994 | |
| WO | WO 95/07077 | 3/1995 | |
| WO | WO 96/14899 | 5/1996 | |
| WO | WO 96/39188 | 12/1996 | .......... A61K/41/00 |
| WO | WO 96/41579 | 12/1996 | |
| WO | WO 97/00098 | 1/1997 | |
| WO | WO 98/33444 | 8/1998 | |
| WO | WO 98/52610 | 11/1998 | .......... A61K/41/00 |
| WO | WO 98/53847 | * 12/1998 | .......... A61K/38/28 |

OTHER PUBLICATIONS

International Search Report, Jul. 12, 2000.
Konig, K., et al., "Photodynamically Inactivation of Propionibacterium Acnes" (1998) SPIE, vol. 3247; 106–110.
Koenig, K., et al., "Photodynamically Induced Inactivation of Propionibacterium Acnes Using the Photosensitizer Methylene Blue and Red Light" (1992) Dermatol. Monatsschr., vol. 178; 297–300.

(List continued on next page.)

Primary Examiner—Brian L. Casler
Assistant Examiner—Jennifer Maynard
(74) Attorney, Agent, or Firm—Nutter McClennen & Fish LLP

(57) ABSTRACT

Laser treatments of sebaceous gland disorders with laser sensitive dyes are disclosed. A preferred laser treatment includes topical application of an energy activatable material to the skin followed by laser irradiation.

7 Claims, 9 Drawing Sheets

(3 of 9 Drawing Sheet(s) Filed in Color)

U.S. PATENT DOCUMENTS

| | | | | |
|---|---|---|---|---|
| 5,422,093 | A | | 6/1995 | Kennedy et al. ............ 424/9.61 |
| 5,423,803 | A | | 6/1995 | Tankovich et al. .............. 606/9 |
| 5,425,728 | A | | 6/1995 | Tankovich ...................... 606/9 |
| 5,445,611 | A | * | 8/1995 | Eppstein et al. ............... 604/49 |
| 5,464,436 | A | | 11/1995 | Smith |
| 5,520,905 | A | | 5/1996 | Uhlmann et al. |
| 5,647,866 | A | | 7/1997 | Zaias et al. ..................... 606/9 |
| 5,669,916 | A | * | 9/1997 | Anderson .................... 606/133 |
| 5,713,845 | A | | 2/1998 | Tankovich .................... 604/20 |
| 5,733,572 | A | * | 3/1998 | Unger et al. ................. 424/450 |
| 5,735,844 | A | * | 4/1998 | Anderson et al. ............... 606/9 |
| 5,752,948 | A | | 5/1998 | Tankovich et al. .............. 606/9 |
| 5,752,949 | A | | 5/1998 | Tankovich et al. .............. 606/9 |
| 5,817,089 | A | * | 10/1998 | Tankovich et al. .............. 606/9 |
| 5,856,566 | A | | 1/1999 | Golub |
| 5,925,034 | A | | 7/1999 | Buckley et al. |
| 5,955,490 | A | * | 9/1999 | Kennedy et al. ............ 514/410 |
| 6,036,684 | A | | 3/2000 | Tankovich et al. |
| 6,063,108 | A | | 5/2000 | Salansky et al. |
| 6,165,170 | A | | 12/2000 | Wynne et al. |
| 6,168,590 | B1 | | 1/2001 | Neev |
| 6,283,956 | B1 | * | 9/2001 | McDaniel ....................... 606/9 |
| 6,306,130 | B1 | * | 10/2001 | Anderson et al. ............. 606/27 |
| 6,358,272 | B1 | | 3/2002 | Wilden |

OTHER PUBLICATIONS

Dierickx, C.C., et al., "Photodynamic Therapy for Nevus Sebaceus with Topical Delta Aminolevulinic Acid" (1999) Archives of Dermatology, vol. 135; 637–640.

Konig, K., et al., "Photodynamic Activity of Methylene Blue" (1993) Aktuelle Dermatologie, vol. 19; 195–198.

Phillips, T.J. and Dover, J.S., "Recent Advances in Dermatology", *The New England Journal of Medicine*, vol. 326, No. 3:167–178 (Jan. 16, 1992).

Rosacea, "Pathophysiology and Treatment", *Arch Dermatol*, vol. 130:359–362 (3/94).

Mutzhas, et al. "A New Apparatus with High Radiation Energy Between 320–460nm: Physical Description and Dermatological Applications" *The Journal of Investigative Dermatology*, vol. 76 pp. 42–47 (1981).

Gfesser, et al. "Seasonal Variations in the Severity of Acne Vulgaris" *International Journal of Dermatology*, vol. 35, No. 2, pp. 116–117 (1996).

Sigurdsson et al. "Phototherapy of Acne Vulgaris with Visible Light" *Dermatology*, vol. 194, pp. 256–260 (1997).

Arakane et al. "Singlet Oxygen Generation from Coproporphyrin in Propionibacterium acnes on Irradiation" *Biochemical and Biophysical Research Communications*, vol. 223, article 0937, pp. 578–582 (1996).

Kjeldstad et al. "Changes in Polyphosphate Composition and Localization in Propionibacterium Acnes After Near–Ultraviolet Irradiation" *Can J. Microbiol*, vol. 37, pp. 562–567 (1991).

Naess et al. "In Vivo and in Vitro Effects of Doxycycline on Leucocyte Membrane Receptors".

*Clin. exp Immunol*, vol. 62, pp. 310–314 (1985).

Kollias, et al. "Endogenous Skin Fluorescence Includes Bands that may Serve as quantitative Markers of Aging and Photoaging" *The Journal of Investigative Dermatology*, vol. 111, No. 5, pp. 776–780 (1998).

Brookner, et al., "Safety Analysis: Relative Risks of Ultraviolet Exposure from Fluorescence Spectroscopy and Colposcopy Are Comparable" *Photochemistry and Photobiology*, vol. 65, No. 6 pp. 1020–1025 (1997).

Mills, et al. "Ultraviolet Phototherapy and Photochemotherapy of Acne Vulgaris" *Arch Dermatol*, vol. 114, pp. 221–223 (1978).

* cited by examiner

TARGETING OF SEBACEOUS FOLLICLES AS A TREATMENT OF SEBACEOUS GLAND DISORDERS

CROSS-REFERENCE TO RELATED APPLICATIONS

This application is a continuation-in-part of U.S. patent application Ser. No. 09/225,026, filed Jan. 4, 1999, now U.S. Pat. No. 6,183,773, the contents of which are incorporated herein by reference.

BACKGROUND OF THE INVENTION

Skin disorders, such as acne, can be irritating and embarrassing. The major disease of skin associated with sebaceous follicles, is acne vulgaris. This is also the most common reason for visiting a dermatologist in the United States. There are many treatments, but no cures for acne. These include antibiotics (which inhibit growth of p. acnes bacteria which play a role in acne), retinoids such as Accutane® (isotetinoin, which reduces sebaceous gland output of sebum), and antimicrobials such as benzoyl peroxide. Acne lesions result from the rupture of a sebaceous follicle, followed by inflammation and pus (a "whitehead"), or by accumulation of plugged material in the sebaceous follicle (a "blackhead"). This pathophysiology has two major requirements: (1) plugging of the upper portion of the follicle, and (2) an increase in sebum production. The upper portion of the follicle, i.e., the "pore" into which sebum is secreted and which is directly in communication with the skin surface, is called the infundibulum. A plug forms in the infundibulum from cells, sebum, bacteria, and other debris. The sebaceous gland continues to produce sebum (an oily fluid), stretching the infundibulum until either it or some lower portion of the follicles ruptures.

Generally, only a minority of sebaceous hair follicles on the face and upper back develop acne lesions. Therefore, it is likely that some structural differentiation predisposes a fraction of the follicles to develop acne. In most males, acne is worst in the teenage years and then subsides, suggesting that a subpopulation of follicles may be present which ultimately self-destruct. In women, teenage acne is often followed by menstrual acne flares well into adulthood. Since both plugging of the infundibulum and high sebaceous gland activity are necessary for an acne lesion to develop, it is likely that the predisposing factors for the follicles which become infected are (1) an infundibulum shape which is easily plugged, and/or (2) a hyperactive sebaceous gland.

Unlike medical dermatology, most laser dermatology treatments are actually "cures"—producing a permanent anatomic, microsurgical effect on the skin. This includes skin resurfacing, portwine stain treatment, tattoo and pigmented lesion removal, and hair removal. Selective photothermolysis or controlled skin ablation with lasers or other extremely intense light sources, might therefore be capable of curing skin disorders, such as acne, if appropriately targeted to the primary site(s) of pathophysiology.

SUMMARY OF THE INVENTION

The present invention is based, at least in part, on the discovery that energy activatable materials, such as chromophores, described infra, in combination with an energy source, e.g., photo (light) therapy, can be used to treat sebaceous gland disorders, e.g., eliminate, inhibit, or prevent occurrence or reoccurrence of the skin disorder. A preferred example of such a sebaceous gland disorder is acne.

The present invention pertains to methods for treating skin disorders associated with sebaceous follicles by topically applying an energy activatable material to a section of skin afflicted with a sebaceous gland disorder, wherein the material is activated by energy which penetrates outer layers of epidermis. A sufficient amount of the material infiltrates the afflicted section of skin and is exposed to sufficient energy to cause the material to become photochemically or photothermally activated, thereby treating the sebaceous gland disorder. In one embodiment, the sebaceous gland disorder is acne. Suitable energy sources include flash lamp based sources and lasers, such as Nd: YAG, Alexandrite, flash lamp-pumped dyes and diodes. Alternatively, the energy source can also be a continuous wave energy source. In preferred embodiments, the energy activatable material is a laser sensitive chromophore, e.g., a chromophore which is capable of being photostimulated by a laser, e.g., a dye. In a particularly preferred embodiment, the chromophore is methylene blue.

The present invention also pertains to methods for modifying the opening to the infundibulum by topically applying an energy activatable material to the opening to the infundibulum, wherein the material is activated by energy which penetrates outer layers of epidermis. Preferably, the perfusion of the material into the pore opening and/or sebaceous gland is increased by iontophoresis. A sufficient amount of the material infiltrates spaces about the infundibulum and the infundibulum is exposed to sufficient energy to cause the material to become photochemically or photothermally activated, thereby modifying the opening to the infundibulum. In one embodiment, the opening to the infundibulum is enlarged. In another embodiment, the opening to the infundibulum is decreased. In still another embodiment, the opening to the infundibulum is altered such that pore pluggage will not occur, e.g., the infundibulum is reshaped such that excess sebum, oils, dirt and bacteria will not cause pore pluggage to occur, resulting in a black head (comedon) or white head (milium).

The present invention also pertains to methods for down regulating, e.g., decreasing, the oil/lipid output production of the sebaceous gland. Application of the energy activatable material to the pilosebaceous unit, e.g., the sebaceous gland, followed by stimulation by an energy source can cause selective permanent physical alteration to the sebaceous gland and/or follicle such that surrounding tissue remains unaffected. The physical alteration to the sebaceous gland and/or follicle results in diminished production of sebum.

The present invention further pertains to methods for modifying the pilosebaceous unit by topically applying an energy activatable material to the pilosebaceous unit, wherein the material is activated by energy which penetrates into the dermis and into the outer layers of epidermis. A sufficient amount of the material infiltrates the pilosebaceous unit and the pilosebaceous unit is exposed to sufficient energy to cause the material to become photochemically or photothermally activated, thereby modifying the pilosebaceous unit. In one embodiment, the pilosebaceous unit is treated such that sebum production is diminished. A decrease in pore pluggage can occur, as a result of the diminishment of sebum production. In one preferred embodiment, treatment of the pilosebaceous unit by the present invention results in elimination of pore pluggage, e.g., the pilosebaceous unit is treated such that excess sebum, oils, dirt and bacteria will not cause pore pluggage to occur, resulting in a black or white head.

BRIEF DESCRIPTION OF THE DRAWINGS

The file of this patent contains at least one drawing executed in color. Copies of this patent with color drawings will be provided by the Patent and Trademark Office upon request and payment of the necessary fee.

DETAILED DESCRIPTION OF THE INVENTION

Figure 1:
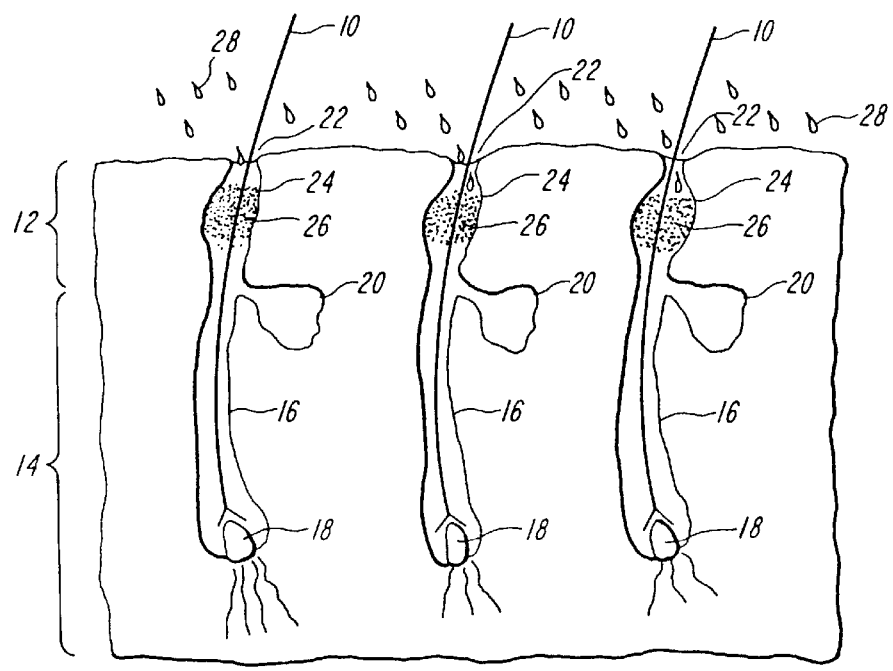
FIG. 1 is a cross-sectional view of hair shafts with pore pluggage and energy activatable material.

The features and other details of the invention will now be more particularly described and pointed out in the claims. It will be understood that the particular embodiments of the invention are shown by way of illustration and not as limitations of the invention. The principle features of this invention can be employed in various embodiments without departing from the scope of the invention.

The present invention is based, at least in part, on the discovery that energy activatable materials, such as chromophores, described infra, in combination with an energy source, e.g., photo (light) therapy, can be used to treat sebaceous gland disorders, e.g., eliminate, remove, or prevent occurrence or reoccurrence of the sebaceous gland disorder. Examples of such sebaceous gland disorders include sebaceous gland hyperplasia, acne vulgaris and acne rosacea. A preferred example of such a sebaceous gland disorder is acne.

In one aspect, the present invention is drawn to methods for treating sebaceous gland disorders by topically applying an energy activatable material to a section of skin afflicted with a sebaceous gland disorder. The energy activatable material is energetically stimulated by an energy source. For example, the energy activatable material can be a chromophore which absorbs at least one frequency band of energy which penetrates outer layers of epidermis. A sufficient amount of the material infiltrates the skin and the section of skin is exposed to at least one frequency band of energy so as to impart, to the material, sufficient energy to cause the material to become photochemically or photothermally activated which brings about a physiological change, thereby treating the sebaceous gland disorder. In one embodiment, the sebaceous gland disorder is acne. Suitable energy sources include a wide range of electromagnetic sources including, energy emitted by the sun, Rf (radio frequency) energy, energy from microwave generators, ultraviolet light generators, flash lamp based sources and lasers, such as Nd: YAG, Alexandrite, and flash lamp-pumped dyes and diodes. Alternatively, the energy source can be a continuous wave energy source. In preferred embodiments, the energy activatable material is a laser sensitive chromophore, e.g., a chromophore which is capable of being photostimulated by a laser. In a particularly preferred embodiment, the chromophore is methylene blue.

The present invention also pertains to methods for modifying the opening to the infundibulum by topically applying an energy activatable material to the opening to the infundibulum, wherein the material absorbs at least one frequency band of energy which penetrates outer layers of epidermis. A sufficient amount of the material infiltrates spaces about the infundibulum and the section of skin is exposed to at least one frequency band of energy so as to impart to the material, sufficient energy to cause the material to become photochemically or photothermally activated, thereby modifying the opening to the infundibulum. In one embodiment, the opening to the infundibulum is altered such that pore pluggage will not occur, e.g., the infundibulum is reshaped such that excess sebum, oils, dirt and bacteria will not cause pore pluggage to occur, resulting in a blackhead (comedon) or white head (milium). In a preferred embodiment, the opening to the infundibulum is opened.

The present invention further pertains to methods for modifying the pilosebaceous unit by topically applying an energy activatable material to the pilosebaceous unit, wherein the material absorbs at least one frequency band of energy which penetrates outer layers of epidermis. A sufficient amount of the material infiltrates the pilosebaceous unit and the section of skin is exposed with at least one frequency band of energy so as to impart to the material, sufficient energy to cause the material to become photochemically or photothermally activated, thereby modifying the pilosebaceous unit. In one embodiment, the pilosebaceous unit is treated such that sebum production is diminished, thereby resulting in decreased pore pluggage. In one preferred embodiment, treatment of the pilosebaceous unit by the present invention results in elimination of pore pluggage, e.g., the pilosebaceous unit is treated such that excess sebum, oils, dirt and bacteria will not cause pore pluggage to occur, resulting in a black or white head.

Sebaceous glands are components of the pilosebaceous unit. They are located throughout the body, especially on the face and upper trunk, and produce sebum, a lipid-rich secretion that coats the hair and the epidermal surface. Sebaceous glands are involved in the pathogenesis of several diseases, the most frequent one being acne vulgaris. Acne is a multifactorial disease characterized by the occlusion of follicles by plugs made out of abnormally shed keratinocytes of the infundibulum (upper portion of the hair follicle) in the setting of excess sebum production by hyperactive sebaceous glands. Various treatment modalities for acne exist that aim in modifying the rate of sebum secretion by the sebaceous glands (e.g., retinoids), inhibiting the bacterial overgrowth in the follicular duct (antibiotics), or decreasing the inflammation of acne lesions (anti-inflammatory agents). Most of these agents are not curative of acne and simply control the disease by affecting one of the aforementioned pathogenic factors. Oral retinoids are a notable exception: they are potent drugs that can achieve a significant cure rate for acne, but their side effect profile often limits their use.

Advantages of the present invention include that treatment can permanently alter the pilosebaceous unit, rendering it no longer susceptible to pore pluggage without the side effects associated with oral retinoids.

The term "sebaceous gland disorders" is intended to include those sebaceous gland disorders which can be treated by an energy activatable material. The energy activatable material can be a photothermally or photochemically activatable, e.g., reactive, material which is susceptible to photoactivation or stimulation, e.g., light, i.e., laser stimulation. The activation or excitation of the material generates reactive species, such as radicals, which can interact with the site of pore pluggage, inflammation, bacteria, viruses, etc. and promote, for example, oxidation of those agents which are associated with the disorder. Examples of sebaceous gland disorders which can be treated by the methods of the invention include sebaceous gland hyperplasia, acne vulgaris and acne rosacea. Of particular importance is treatment of acne by the method of the invention.

The term "pluggage" is intended to obstruction of the pores by the buildup of sebum, dirt, bacteria, mites, oils, and/or cosmetics in the pore, e.g., about the infundibulum.

The term "acne" is art recognized and is intended to include acne vulgaris and acne rosacea. Acne vulgaris the most common skin disease seen in dermatologic practice which affects approximately 17 million people in the United States. Its precise cause is unknown, although abnormal keratin production with obstruction of the follicular opening, increased production of sebum (lipids secreted by the androgen-sensitive sebaceous glands), proliferation of *Propionibacterium acnes* (anaerobic follicular diphtheroids), follicular rupture and follicular mites (demodex) are commonly associated with acne.

Skin conditions such as acne are believed to be caused or exacerbated by excessive sebum flow produced by sebaceous glands most of which are adjacent to and discharge sebum into, hair follicles. Sebum is composed of keratin, fat, wax and cellular debris. Sebum forms a moist, oily, acidic film that is mildly antibacterial and antifungal and may to some extent protect the skin against drying. It is known that the bacteria which contribute to acne, *Propionibacterium acnes* or (P-acnes), grows in sebum. Significant sebum flow in humans begins at puberty. This is when acne problems generally arise.

The phrase "energy activatable material" is intended to include those agents which, when stimulated by energy from an energy source, e.g., a laser source, become energetically stimulated, e.g., photothermally or photochemically. These materials can be stimulated by various energy sources, e.g., electromagnetic sources, such as a continuous wave source, a laser source, flashlamp, ultraviolet light, microwaves, infrared light, etc. The material absorbs the energy which causes the material to become thermally or chemically active.

Suitable materials useful in the invention include metal oxides, such as aluminum oxide, iron oxides, carbon particles (graphite and amorphous carbon particles) and natural and synthetic chromophores. The term "chromophore" is art recognized and is intended to include those compounds which absorb energy at a given wavelength, often by sites of unsaturation, carbon-oxygen bonds, and/or charged species, or combinations thereof. Suitable chromophoric groups include nitro groups, azo, quinoids, alkylene units, carbonyls, esters, alkynes, aldehydes, carboxylic acids, and those groups associated with n®π* and π®π* transitions. Preferred energy activatable materials include laser sensitive dyes, for example, methylene blue, indocyanine green and those in U.S. Pat. No. 4,651,739, issued Mar. 24, 1987, the entire contents of which are incorporated herein by reference. Preferred dyes are those dyes which are activated by laser stimulation. Preferred laser sensitive dyes are those which are FDA approved. A preferred dye, a laser sensitive dye, is methylene blue. In one embodiment, the laser sensitive dye is not indocyanine green. In another embodiment, the energy activatable material is not carbon particles.

The energy activatable materials of the present invention undergo energetic activation, by photothermal or photochemical stimulation. The term "photothermal" interaction (excitation or stimulation) is art recognized and is intended to include interactions which are due to conversion of energy into heat. Photothermal activation of an energy activatable material causes the material to be heated, thereby heating the local area, preferably selectively with a significant temperature increase of such that unwanted material, e.g., tissues, oils, bacteria, viruses, dirt, etc. such that the surrounding tissue remains unaffected The photothermally activated material can form biologically reactive products. Photothermal processes can involve oxidation of, for example, cell walls, extracellular matrix components, nuclei, etc. As a result of photothermal stimulation, the infundibulum can be reshaped as a result of collagen shrinkage. Additionally, the process can cause cell death in the sebaceous gland, thereby decreasing production of sebum.

The term "photochemical" is art recognized and is intended to include molecular bond breaking where one or more absorbed photon excites the molecule to a higher electronic, vibrational, or rotational state. Photochemical stimulation of an energy activatable material causes the material to enter an excited energy state wherein energy is absorbed, e.g., by the chromophore, whereby bonds within the energy activatable material are broken and forms reactive by products such as radical species. These reactive by products can interact with the localized surrounding tissue area such that the tissue is cleansed of unwanted material, e.g., oils, bacteria, viruses, dirt, etc. As a result of photochemical stimulation, the infundibulum can be reshaped as a result of collagen shrinkage. Additionally, the photochemical process can cause cell death in the sebaceous gland, thereby decreasing production of sebum.

The photochemically activated material can return to the ground state or it can decompose into biologically reactive fragments. Photochemical processes can involve oxidation or radical polymerization of, for example, cell walls, extracellular matrix components, nuclei, etc.

Photochemical activation of energy activatable materials can be achieved over long time periods with energy of low intensity. For example, treatment of sebaceous gland disorders could be treated with an energy activatable material contained in a cream or lotion applied to the skin prior to long periods of exposure to the sunlight, e.g., while participating in sports or sitting on the beach.

The energy activatable materials of the present invention do not undergo fragmentation or vaporization such that the energy activatable material causes photo-mechanical destruction of the surrounding tissue, e.g., the energy activatable materials do not undergo violent decomposition, i.e., the energy activatable materials do not explode. Preferably, therefore, the energy activatable material is subjected to a sufficient energy which causes the energy activatable material to be photochemically or photothermally stimulated without violent decomposition and harm to surrounding tissue (See for example Ton G. van Leeuwen et al. Optical- Thermal Response of Laser-Irradiated Tissue, "Pulsed Laser Ablation of Soft Tissue" ed. A. J. Welch and M. J. C. van Gemert, Chapter 21, pg 709, Plenum Press, New York, 1995).

Not to be limited by theory, stimulation of the energy activatable material, e.g., a chromophoric agent, can cause oxidation and decomposition of the unwanted material(s), thereby degrading and removing unwanted material from the pore. Additionally, this treatment can also cause the opening to the infundibulum to become modified, e.g., the pore opening is enlarged or the pore opening is constricted or closed. Consequently, alteration of the pore opening, such as enlargement of the pore opening, a change in the pore shape, or constriction of the pore opening prevents unwanted dirt, bacteria, viruses and/or oils from building up in the treated area, e.g., the infundibulum.

Photothermal alteration of the sebaceous gland, the follicle infundibulum, or both requires the deposition of sufficient energy to cause local heating to temperatures capable of cell killing (e.g., killing of sebocytes, stem cells, or bacterial cells), protein denaturation (e.g., denaturation of basement membranes and/or perifollicular collagen), or vaporization of tissue. In general, these temperatures range from about 60–100° C. for the first two effects, and somewhat over 100° C. (e.g., about 120° C.) for vaporization of tissue.

The amount of a light-absorbing dye which must be present for a given local fluence of a pulse of optical energy to cause these photothermal effects, can be determined by considering the basic principles of selective photothermolysis. If the pulse of optical radiation is delivered within the thermal relaxation time for the target structure, heat flow from the target is limited during the pulse. The preferred pulse duration is therefore about equal to or less than the thermal relaxation time of the given target, which measured in seconds is approximately equal to the square of the target's shortest dimension measured in millimeters. For example, the infundibulum portion of most sebaceous follicles on the face is approximately 0.3 mm in diameter, which corresponds approximately to a thermal relaxation time of about 0.1 seconds (100 ms). The sebaceous gland is similar in diameter, but may on the nose be as large as 1 mm. Although thermal confinement is achieved with pulses shorter than the target's thermal relaxation time, very short pulses cause unwanted mechanical injury which can rupture the follicles. For example, the method of Tankovich, U.S. Pat. Nos. 5,752,949, 5,425,728, 5,226,907 and 5,752,948, employs explosive, photomechanical mechanism to damage hair follicles. Skin eruption has been observed on patients with an acne-like skin caused by the Tankovich treatment.

The fatty acids, sebum, and bacteria present in sebaceous follicles is extremely irritating if not contained by the follicle. In acne vulgaris, rupture of the follicle is the event which stimulates inflammation to form a "pimple", including accumulation of pus to form a "whitehead". It is therefore desired to avoid rupture of the follicle or sebaceous gland. Such mechanical injury can be avoided by using pulses longer than about 0.1 milliseconds. Thus, the preferred range of pulse duration is 0.1–100 ms, and the ideal pulse duration is about 10–50 ms.

When thermal confinement during the pulse is achieved, the local temperature rise is given approximately by $\Delta T = E\mu(\rho c)^{-1}$, where E is the local fluence at the target, $\mu$ is the local absorption coefficient of the target, and $\rho c$ is heat capacity of the target. It is highly preferred to use wavelengths of the optical spectrum in which natural skin pigments exhibit weaker absorption (to minimize heating at other sites), and which penetrate well to the anatomic depth of the infundibulum and/or sebaceous glands. The orange, red, and near-infrared wavelength region (600–1200 nm) is therefore most appropriate. At these wavelengths, there is very little absorption by natural skin pigments other than melanin.

Melanin is often present in coarse hairs, but in general is absent or nearly absent in the vellus hairs present in the sebaceous follicles associated with acne vulgaris. The exception to this is when a "blackhead" (an open comedo) is present, which consists of a plugged sebaceous follicle containing melanin or melanin-like oxidized substances which absorb light. To a reasonable approximation, therefore, there is no optical absorption in the 600–1200 nm wavelength region in most sebaceous follicles. The tolerable fluence for human skin of an optical pulse in this part of the spectrum is about 5–100 J/cm², depending on the amount of epidermal melanin and on wavelength. Skin surface-cooling methods can also be used to increase this tolerable fluence. Ideally, an amount of dye can be taken up by the sebaceous follicle such that a pulse delivering less than 100 J/cm² can produce desired photothermal effects. The target absorption coefficient, $\mu$ is approximately equal to 2.3, times the local molar concentration [d] of the dye in the follicle, times the molar extinction coefficient $\epsilon$ for that dye. The value of $\rho c$ for most tissues is about 4 Jcm$^{-3}$C$^{-1}$. Many dyes have molar extinction coefficients of $10^3$–$10^5$ M$^{-1}$cm$^{-1}$.

From this information, the local dye concentration needed in the follicle can be estimated, and used to direct therapy. For example, to reach a temperature of approximately 80° C., a temperature rise $\Delta T$ would be about 50° C. because the ambient skin temperature is typically about 30° C. At a fluence of E=10 J/cm² (easily tolerated by most skin types), the local value of $\mu$ must therefore be about $\mu = \Delta T \rho c / E = (50)(4)(10)$, or 20 cm$^{-1}$. The concentration of a dye to achieve this absorption coefficient at the target, can be determined. Preferred dyes such as methylene blue have molar extinction coefficients about $\epsilon = 10^4$ M$^{-1}$cm$^{-1}$, which require uptake to a dye concentration [d] in the follicle of about $[d] = \mu/(2.3\epsilon) = 20/(2.3 \times 10^4)$, or about $10^{-3}$M.

Thus, about 1 mM concentration of these dyes is sufficient to achieve the desired photothermal effects to inhibit acne vulgaris. Because a factor of 10 was allowed in the tolerable fluence in the above example, it would be possible (minimally) to practice the invention with values of $\mu$ as low as about 2 cm$^{-1}$, corresponding to dye concentration of about 0.1 mM (100 $\mu$M). However, it is preferred in practice to provide a safety margin between the fluence necessary for the desired photothermal effect on sebaceous glands and/or infundibulum, and the maximum fluence tolerated by human skin. The preferred dye concentration in the follicle infundibulum and/or sebaceous gland is therefore greater than 0.1 mM for most of the preferred dyes, and more generally a sufficient concentration to achieve a local absorption coefficient of greater than about 10 cm$^{-1}$.

Preferably, the energy source produces an exposure area of between about 3 to about 100 millimeters to treat a section of skin afflicted with a sebaceous gland disorder, as described above. The fluence is limited such that the skin is not damaged while the sebaceous gland disorder is treated, e.g., eradicated, inhibited, or prevented. The fluence is controlled such that localized destruction to the undesired sebaceous gland disorder occurs with little or no non-specific necrosis of surrounding tissue. For example, at 755 nm, up to 100 J/cm² can be administered to a very fair Caucasian individual without damage to the skin. The amount of energy a darker skin could tolerate without damage to the skin would be less. A person having skill in this art can ascertain the amount of energy and type of energy to be expended to achieve the results desired.

Suitable energy sources include light-emitting diodes, incandescent lamps, xenon arc lamps, lasers or sunlight. Suitable examples of continuous wave apparati include, for example, diodes. Suitable flash lamps include, for example pulse dye lasers and Alexandrite lasers. Representative lasers having wavelengths strongly absorbed by chromophores, e.g., laser sensitive dyes, within the epidermis and infundibulum but not sebaceous gland, include the short-pulsed red dye laser (504 and 510 nm), the copper vapor laser (511 nm) and the Q-switched neodymium (Nd): YAG laser having a wavelength of 1064 nm that can also be frequency doubled using a potassium diphosphate crystal to produce visible green light having a wavelength of 532 nm. Further examples of lasers which are suitable for use as energy sources include those in the following table of lasers:

Types of Laser

Commercial Laser Types, Organized by Wavelength

| Wavelength, μm | Type | Output type and power |
| --- | --- | --- |
| 0.523 | Doubled Nd-YLF | Pulsed, watts |
| 0.532 | Doubled Nd-YAG | Pulsed to 50 W or CW to watts |
| 0.534, 0.538 | He—Cd | CW, milliwatts, in white-light laser |
| 0.5435 | He—Ne | CW, 1-mW range |
| 0.578 | Copper vapor | Pulsed, tens of watts |
| 400–700 nm | Pulsed Dye | tens of Joules |
| 514.5 nm | Ar Ion | tens of watts |
| 530.9 nm | Kr Ion | approximately 5 watts |
| 750–900 nm | GaAlAs semiconductor diode array | tens of watts depending on number of elements |
| 1060 nm | Nd:YAG | tens of watts |

Another desirable property of thermal and photochemical energy activatable material is an absorption spectrum in the range of 600–1300 nm; this minimizes surrounding blood from absorbing light intended for the material (hemoglobin absorbs most strongly at the violet end of the spectrum).

The depth of penetration of the energy, e.g., light, emitted from the energy source, such as a laser, is dependent upon its wavelength. Wavelengths in the visible to near IR have the best penetration and are therefore best for use to treat the sebaceous gland and infundibulum located within the dermis.

Photochemical cell killing preferably uses chromophores with peak absorbance in the 600–1300 nm range. Whether photostability is important depends on the mechanism of photochemical cell killing. For example, chromophores which kill by the interaction with oxygen to produce singlet state oxygen, high photostability is desirable, so that such production continues for as long as possible before the chromophore breaks down.

For chromophores which kill by virtue of the degradation of the chromophore to a toxic reaction product, photostability is generally not desired, since the breakdown of the chromophore is the process which achieves the desired effect.

In the present process, selective photoactivation is employed whereby an energy (light) source, e.g., a laser, is matched with a wave-length to the absorption spectrum of the selected energy activatable material, preferably a chromophoric agent, e.g., methylene blue at 661 nm. For example, an energy activatable material, adapted to accumulate selectively in the infundibulum and/or the sebaceous gland, is first applied to the region of afflicted skin to be treated. Following absorption of the energy activatable material, the accumulated material, is exposed to an energy source, e.g., a laser, capable of producing a wavelength readily absorbed by the energy activatable material thereby selectively photothermally heating or photochemically treating those regions of the dermis known to have trapped oils, bacteria, viruses, dirt, etc. i.e., the pilosebaceous unit which includes the pore opening, infundibulum and sebaceous gland. Because the energy activatable material is selectively concentrated within or about these undesired deposits, the deposits are degraded by the heat and/or radical species generated from the energy activated material. There is minimal to no destruction of normal adjacent epidermal and dermal structures.

Preferably, the treatment of the invention modifies the pore opening to the infundibulum such that the geometry, e.g., the shape, of the opening is permanently altered. Adjustment of the concentration of the energy activatable material and the amount of energy applied by the energy source effects constriction, closure, or opening of the pore, thereby preventing accumulation of dirt, oils, bacteria, or viruses in that follicle. The operator will need to assess the parameters to illicit the desired effect and will be determined on a patient by patient basis. Generally, it is most desirable to alter the shape of the pore, leaving the pore enlarged and no longer prone to buildup of sebum and/or foreign materials which would cause pore pluggage.

As previously stated, the present invention involves the use of energy sources, e.g., lasers, to target sebaceous glands and cause their photothermal or photochemical destruction. Sebaceous glands are mainly composed of amorphous lipid material and do not contain any obvious endogenous chromophores. In order to achieve selective photocoagulation of sebaceous glands and confine the extent of thermal injury in the surrounding tissue, a topically applied energy activatable material with selective distribution to the pilosebaceous unit can be utilized. The introduction of a energy activatable material in sebaceous glands followed by exposure to energy (light) with a wavelength that corresponds to the absorption peak of the chromophore, will increase the local absorption of light in tissue and lead to selective thermal damage of sebaceous glands.

The infundibulum is a critical site in the pathogenesis of many of the disease states, especially acne. There is evidence that abnormal proliferation and desquamation of infundibular keratinocytes leads to the formation of microcomedones and, later on, to clinically visible follicular "plugs" or comedones. Clinically, it appears that some sebaceous follicles are more prone than others to develop acne lesions, possibly due to an inherent structural difference or functional abnormality of the infundibulum, that predisposes them to form plugs and occlude. The self-resolving nature of acne in most patients may reflect the elimination of such "acne-prone" follicles which are eventually replaced by normal skin or fibrosis after repeated bouts of inflammation. If the architecture of the infundibulum is important in the pathogenesis of acne, then selective destruction of this portion of the follicle through energy activatable material-assisted energy, e.g., laser, targeting can help eliminate or correct the "pathologic" site by creating a distended follicular opening that is able to extrude any occluded material.

The process of selective energy activation according to the present invention uses energy sources, e.g., light, e.g., lasers, matched to a particular energy activatable material. In the case of photothermal activation, to facilitate temperature rise, the pulse duration time period should be shorter than that of the thermal relaxation time for the energy activatable material. The thermal relaxation time is defined as the time it takes for a structure to cool to 50% of its peak temperature immediately following exposure to a light source capable of providing enough energy to photoactivate the chromophore. Therefore, selective treatment of those dermal regions containing an energy activatable material, e.g., a laser sensitive dye, will occur when exposed to millisecond light pulses. A laser delivering pulses in the range of 1 to 50 milliseconds (ms) has been found to adequately photoactivate energy activatable materials, such as carbon particles, iron oxide particles and laser sensitive dyes, e.g., chromophoric materials, deposited within the hair follicle matrix, e.g., about the infundibulum and sebaceous gland. Different types of energy activatable materials require variations in the energy dose applied and the type of energy source necessary to effect treatment of the afflicted skin area. When applied to the skin of the region to be treated, the energy activatable material is absorbed within the hair follicle matrix and upon exposure, the energy will be concentrated in those critical areas of the follicle matrix where the energy activatable material has collected e.g., the pilosebaceous unit including the sebaceous gland, infundibulum and pore opening.

Delivery of the energy activatable material, preferably methylene blue or other FDA approved dyes, to the follicle matrix can be achieved by topical application, injection, liposome encapsulation technology, massage, iontophoresis or ultrasonic technology, or other means for delivery of compounds into the dermal region of the skin, e.g., pharmaceutically acceptable carriers.

The phrase "pharmaceutically acceptable carrier" as used herein means a pharmaceutically acceptable material, composition or vehicle, such as a liquid or solid filler, diluent, excipient, solvent or encapsulating material, involved in carrying or transporting a energy activatable material of the present invention within or to the subject such that it can performs its intended function. Each carrier must be "acceptable" in the sense of being compatible with the other ingredients of the formulation and not injurious to the patient. Some examples of materials which can serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations. Preferred carriers include those which are capable of entering a pore by surface action and solvent transport such that the energy activatable material is carried into or about the pore, e.g., into the sebaceous gland, to the plug, into the infundibulum and/or into the sebaceous gland and infundibulum.

Wetting agents, emulsifiers and lubricants, such as sodium lauryl sulfate and magnesium stearate, as well as coloring agents, release agents, coating agents, sweetening and perfuming agents, preservatives and antioxidants can also be present in the compositions.

Liquid dosage forms for topical administration of the compounds of the invention include pharmaceutically acceptable emulsions, microemulsions, solutions, creams, lotions, ointments, suspensions and syrups. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor, peach, almond and sesame oils), glycerol, tetrahydrofuryl alcohol, polyethylene glycols and fatty acid esters of sorbitan, and mixtures thereof.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

The term "cream" is art recognized and is intended to include semi-solid emulsion systems which contain both an oil and water. Oil in water creams are water miscible and are well absorbed into the skin, Aqueous Cream BP. Water in oil (oily) creams are immiscible with water and, therefore, more difficult to remove from the skin. These creams are emollients, lubricate and moisturize, e.g., Oily Cream BP. Both systems require the addition of either a natural or a synthetic surfactant or emulsifier.

The term "ointment" is art recognized and is intended to include those systems which have oil or grease as their continuous phase. Ointments are semi-solid anhydrous substances and are occlusive, emollient and protective. Ointments restrict transepidermal water loss and are therefore hydrating and moisturizing. Ointments can be divided into two main groups-fatty, e.g., White soft paraffin (petrolatum, Vaseline), and water soluble, e.g., Macrogol (polyethylene glycol) Ointment BP.

The term "lotion" is art recognized and is intended to include those solutions typically used in dermatological applications.

The term "gel" is art recognized and is intended to include semi-solid permutations gelled with high molecular weight polymers, e.g., carboxypolymethylene (Carbomer BP) or methylcellulose, and can be regarded as semi-plastic aqueous lotions. They are typically non-greasy, water miscible, easy to apply and wash off, and are especially suitable for treating hairy parts of the body.

In a one embodiment, liposomes are used to deliver the energy activatable material to the follicle matrix. Liposomes provide site-specific transdermal delivery to the follicle matrix. In this embodiment, the energy activatable material is microencapsulated within the liposome and topically applied to the epidermis of the skin.

As noted above, the carrier according to the present invention involves encapsulating the effective amount of energy activatable material within a specific liposome to provide for efficient transdermal delivery of the energy activatable material through the layers of the skin. These liposomal compositions are topically applied to the skin and deliver the encapsulated energy activatable material to the follicle region including the sebaceous gland and infundibulum. Following delivery of the energy activatable material, irradiation results in highly specific targeting of the follicle matrix and destruction of oils, dirt, bacteria, mites, or viruses within the infected area.

Liposomes are microscopic spherical membrane-enclosed vesicles or sacks (0.5–500 μm in diameter) made artificially in the laboratory using a variety of methods. Within the scope of the present invention, the liposomes should be non-toxic to living cells and they should deliver the contents, in this case an energy activatable material, into the follicle and immediately surrounding tissue. The liposomes according to the present invention may be of various sizes and may comprise either one or several membrane layers separating the internal and external compartments.

The liposomes may be made from natural and synthetic phospholipids, and glycolipids and other lipids and lipid congeners; cholesterol, cholesterol derivatives and other cholesterol congeners; charged species which impart a net charge to the membrane; reactive species which can react after liposome formation to link additional molecules to the lysome membrane; and other lipid soluble compounds which have chemical or biological activities.

A general discussion of the liposomes and liposome technology can be found in an article entitled, "Liposomes" by Marc J. Ostro, published in *SCIENTIFIC AMERICAN*, January 1987, Vol. 256, pp. 102–111 and in a three volume work entitled, "Liposome Technology" edited by G. Gregorriadis, 1984, published by CRC press, Boca Raton, Fla. the pertinent portions of which are incorporated herein by reference.

Figure 2:
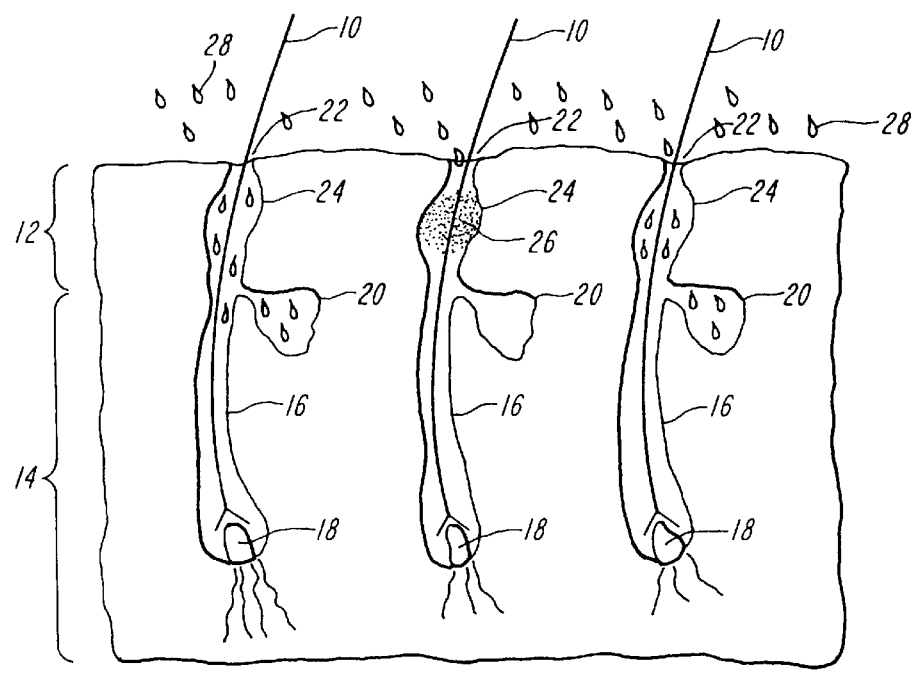
FIG. 2 is a cross-sectional view of a plugged follicle after an energy activatable material has been allowed to penetrate the follicle and sebaceous gland.

FIG. 1 illustrates multiple hair shafts 10 (vellus) projecting below the epidermis region 12 of the skin and into the dermis 14 region. Each shaft 10 extends down the follicle 16. The follicle includes a sebaceous gland 20 and which at the anagen stage of the hair cycle further includes a papilla 18. The papilla 18 is supplied with small blood vessels (not shown) that provide the growing hair with nourishment. The follicle 16 includes the pore opening 22 and the infundibulum 24, shown with a plug 26 of dead cells, oils, bacteria and/or viruses. Topical application of an energy activatable material 28 penetrates the pore opening 22 and infundibulum 24 and into the sebaceous gland 20 as shown in FIGS. 1 and 2.

Figure 3:
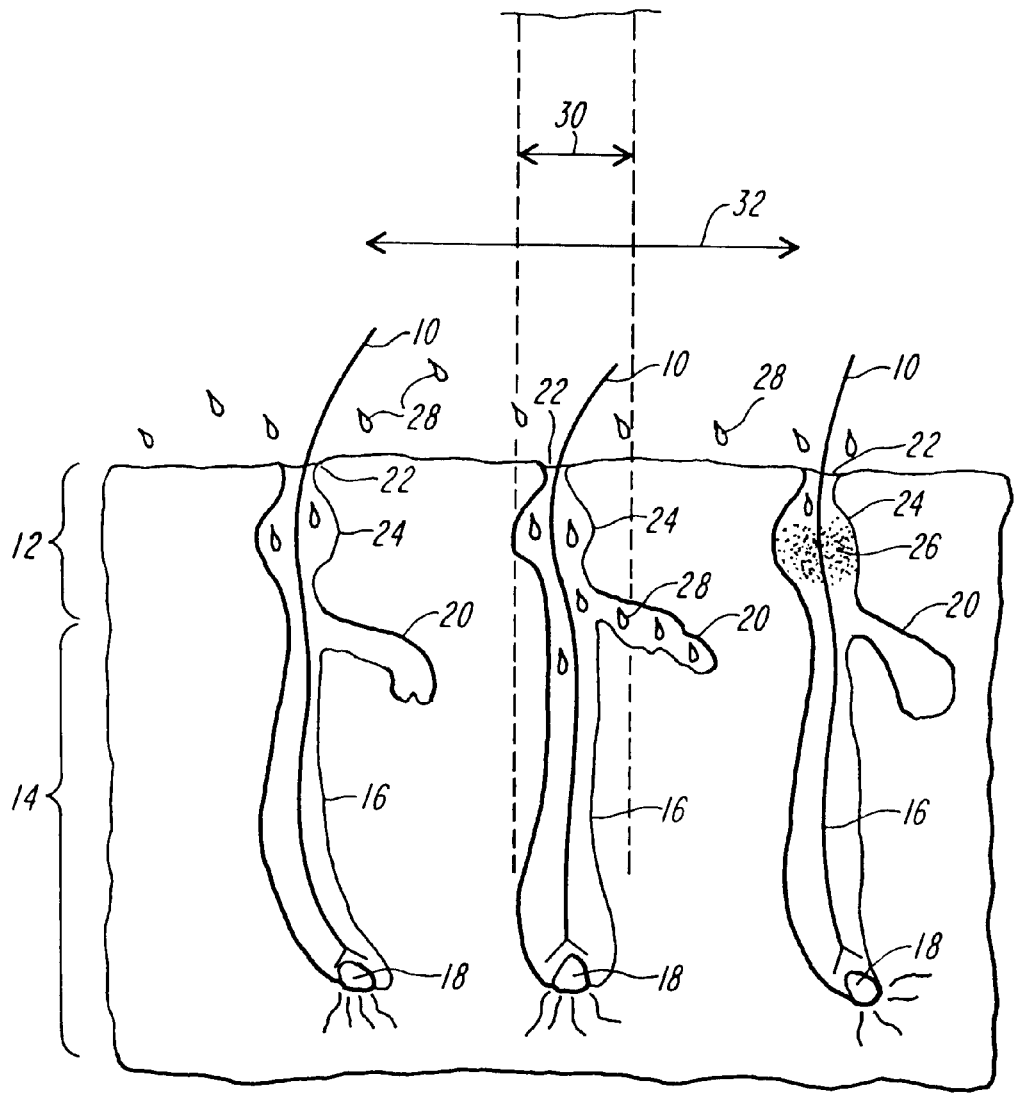
FIG. 3 is a cross-sectional view of hair shafts which include an energy activatable material during irradiation with an energy source, e.g., a laser.

In order to assure removal of plug 26, modification of pore opening 22, modification of the infundibulum 24, and/or modification of the sebaceous gland 20, use of a light source, e.g., a laser, having sufficient energy and depth of penetration is required. FIG. 3 demonstrates how an operator (not shown) will position the energy source 30, e.g., a laser, over a hair follicle 16 such that an optimum location for aiming the light pulse to strike the energy activatable material 28 about the plug 26, sebaceous gland 20, infundibulum 24 and/or pore opening 22 is obtained. The energy source 30 can be moved across the skin surface in any direction 32 by the operator, thereby effectively irradiating multiple follicles 16 multiple times. The process can be repeated until the desired effect(s) are achieved.

Figure 4A:
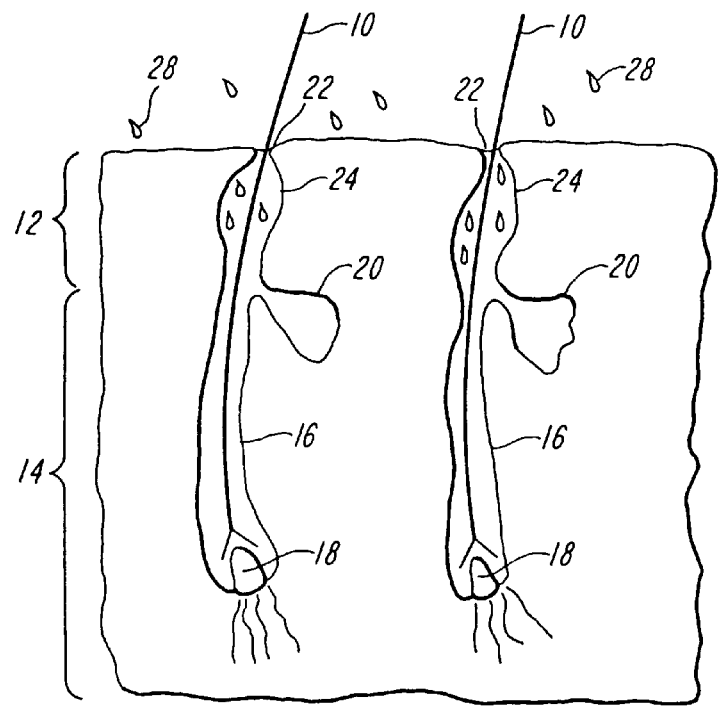
FIGS. 4a and 4b are cross-sectional views of hair shafts where the pore opening and infundibulum are modified by the process of the invention.
Figure 4B:
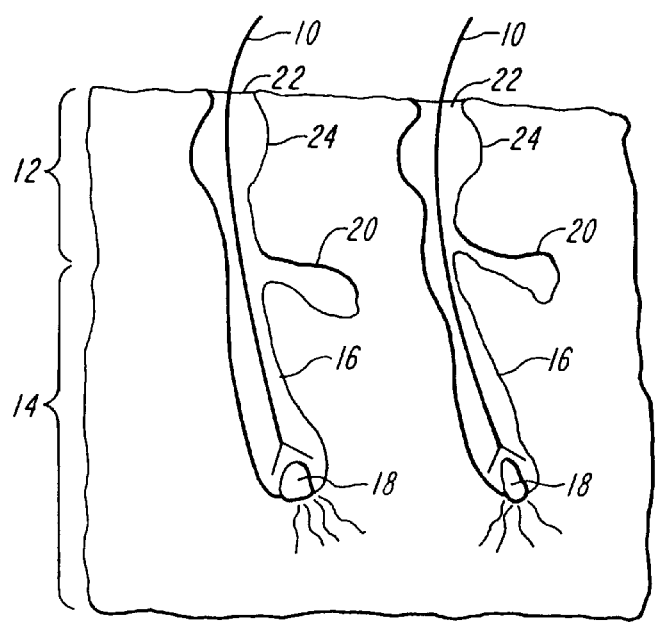

FIGS. 4a and 4b demonstrate the effect(s) of the presently described treatment on the infundibulum 24. FIG. 4a depicts infundibulum 24 prior to treatment with an energy activatable material 28 and stimulation with an energy source 30. FIG. 4b depicts the same infundibulum 24 post treatment whereby the shape of the infundibulum 24 and pore opening 22 have been modified.

Figure 5A:
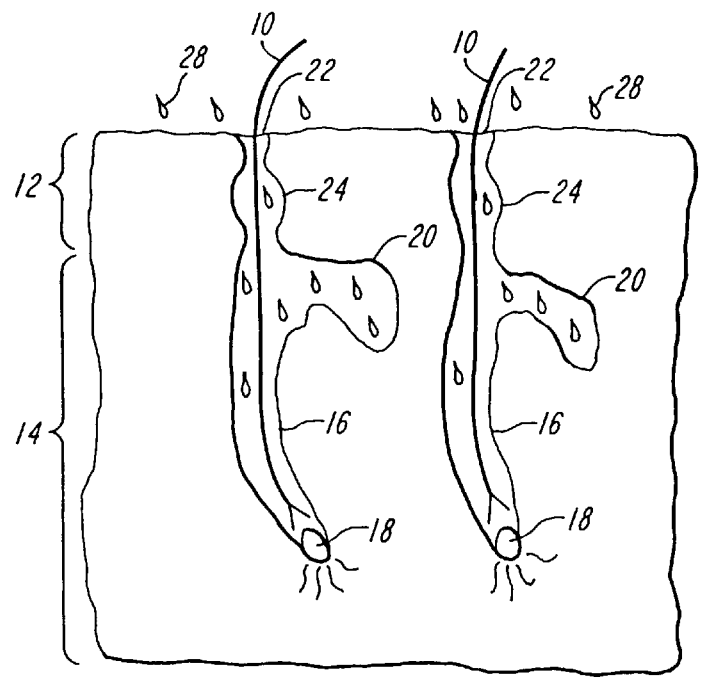
FIGS. 5a and 5b are cross-sectional views of hair shafts where sebaceous glands are modified by the process of the invention.
Figure 5B:
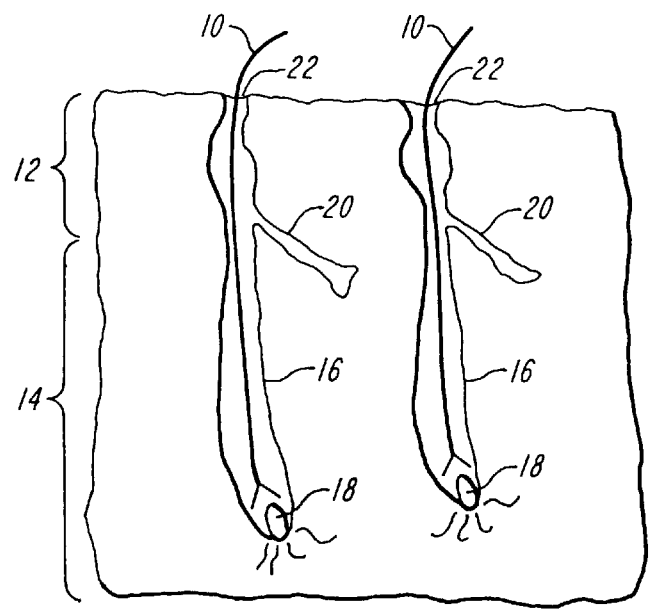

FIGS. 5a and 5b demonstrate the effect(s) of the presently described treatment on the sebaceous gland 20. FIG. 5a depicts the sebaceous gland 20 prior to treatment with an energy activatable material 28 and stimulation with an energy source 30. FIG. 5b depicts the same sebaceous gland 20 post treatment, whereby the size of sebaceous gland 20 has been decreased.

Figure 6A:
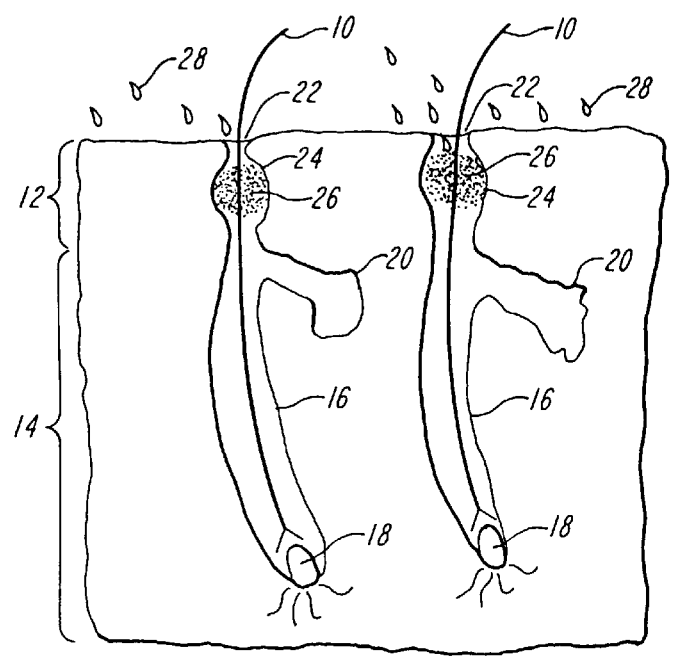
FIGS. 6a and 6b are cross-sectional views of hair shafts where debris within the pore is removed by the process of the invention.
Figure 6B:
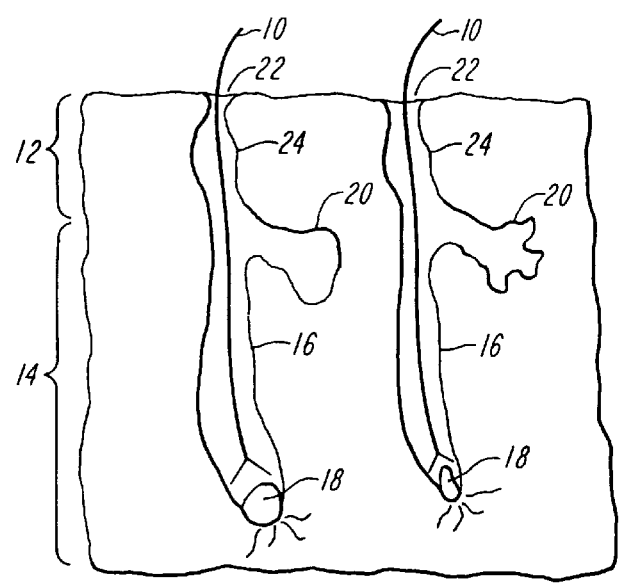

FIGS. 6a and 6b demonstrate the effect(s) of the presently described treatment on a plugged pore 26. FIG. 6a depicts the plug 26 prior to treatment with an energy activatable material 28 and stimulation with an energy source 30. FIG. 6b depicts the same region of the infundibulum 24 post treatment, whereby the plug 26 has been treated such that unwanted material(s) has been removed from infundibulum 24.

Figure 7A:
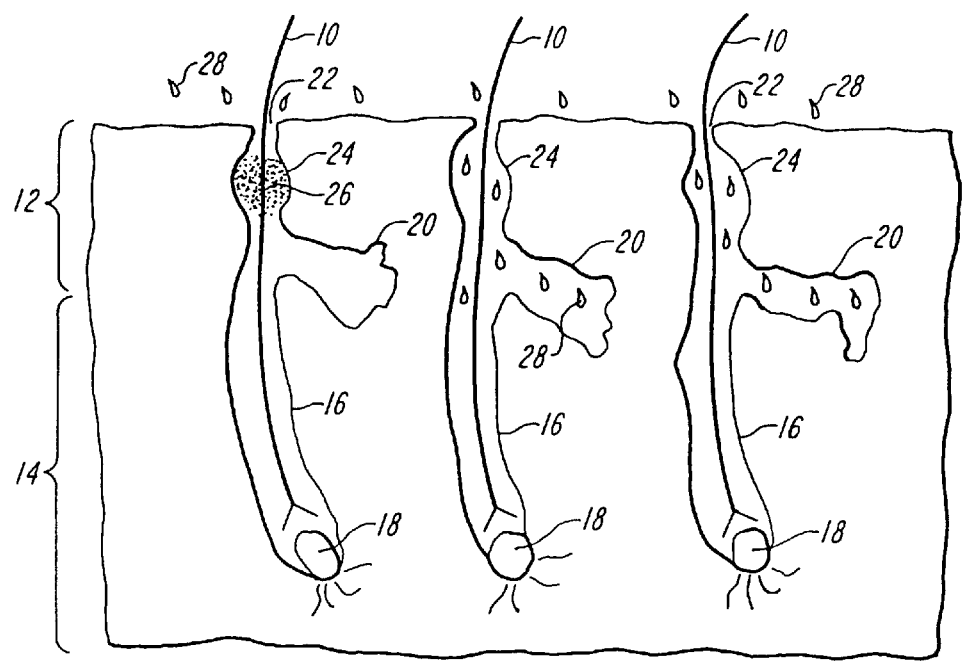
FIGS. 7a and 7b are cross-sectional views of hair shafts where the pore opening, infundibulum and sebaceous glands are modified by the process of the invention and where debris within the pore is also removed.
Figure 7B:
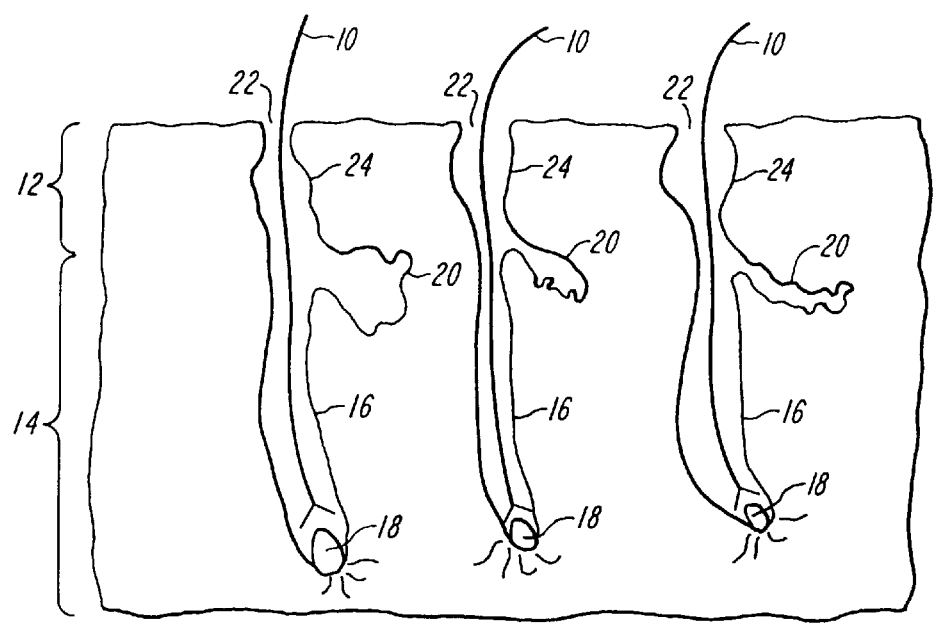

FIGS. 7a and 7b further demonstrate the effect(s) of the presently described treatment on a plugged pore 26, infundibulum 24, pore opening 22, and sebaceous gland 20. FIG. 7a depicts the skin area prior to treatment with an energy activatable material 28 and stimulation with an energy source 30. FIG. 7b depicts the same region of the skin post treatment, whereby the plug 26 has been treated such that unwanted material(s) has been removed from infundibulum 24 and the infundibulum 24, pore opening 22 and sebaceous gland 20 have been modified.

Stimulation of the energy activatable material 28 will cause activation to occur, e.g., photothermolysis and/or photochemical reactions, to disrupt the trapped cells, sebum, bacteria, mites, etc. located in the sebaceous gland 20 and/or the infundibulum 24. An advantage of this process is that only tissue having energy activatable material will undergo photothermal or photochemical reactions. Surrounding tissue which does not include energy activatable material will not be adversely affected by this treatment.

Natural chromophores present in sebaceous follicles or follicular plugs are not sufficiently distinct from other chromophores of the dermis and epidermis to allow specific absorption. However, the infundibulum and sebaceous glands are directly accessible from the skin surface through a "pore" (the follicle opening), which allows topically-applied substances, such as energy activatable materials, to enter these structures. Therefore, energy activatable materials or particle-suspensions can be used to provide high, local, and specific absorption after uptake into the infundibulum and/or sebaceous gland.

Energy activatable materials which enter the sebaceous follicles, such as methylene blue (a lipophilic, cationic, FDA-approved dye is taken up into human sebaceous follicles, and distributed over time into the sebaceous glands), can be used to target either the infundibula, or the sebaceous glands depending on time after application, or both.

Topically-applied energy activatable materials initially enter the infundibulum and later distribute to the sebaceous glands. It is possible to actively drive those materials or chromophoric particles into the follicles by massage, pressure, ultrasound, or iontophoresis, after topically applying the chromophore to the skin surface. Methylene blue, for example, can be rapidly driven into sebaceous follicles and eccrine sweat ducts by iontophoresis. Wiping the surface with or without a solvent after delivery into the follicles, can be used to remove residual material from the skin surface. Thus, after appropriate application and wiping, the energy activatable material, e.g., a chromophore, can be preferentially located in follicles, within the infundibula or the infundibula and sebaceous glands.

A preferred method of delivery for administering an energy activatable material described throughout this application is by iontophoresis. Iontophoresis may be generally described as a method of transdermally introducing medicament ions, zwitterions, molecules, e.g., an energy activatable material, preferably methylene blue, into a the body. The iontophoresis process utilizes the current developed by an electric field to drive energy activatable ions through the skin, or other biological surface, and into the body. The iontophoresis process has been found to be particularly useful in transdermal administration of energy activatable materials, such as many of the compounds discussed herein, and in particular, methylene blue.

For example, and advantage of iontophoresis is the introduction of energy activatable materials directly into a patient's tissues, e.g., the infundibulum and/or sebaceous gland, without the need for a needle-based injection, which typically causes pain and may create a risk of infection. Iontophoretic delivery of energy activatable materials is also advantageous because this delivery system avoids premature metabolism of the material that can typically occur when a drugs is taken orally. Premature metabolism is often a concern where oral drugs are used to treat acne because the medicament ions derived are absorbed into the blood stream from the digestive system. The blood containing the medicament ions then percolates through the liver, where the medicament ions may be prematurely metabolized, before the medicament ions arrive at the target tissue. Thus, a substantial amount of the medicament ions derived from an orally administered drug may be metabolically inactivated before the medicament ions have a chance to pharmacologically act in the body.

A typical iontophoresis device includes two electrodes such as those devices produced by Iomed, Inc. (Salt Lake City, Utah, US). One of the electrodes is often characterized as an "active" electrode, and the other electrode is often characterized as a "return" electrode. Also, one of the electrodes is a positively charged anode and the other electrode is a negatively charged cathode. Both electrodes are in intimate electrical contact with the skin or other biological surface of the body, which may be a human body or another type of body, such as an animal body. Application of electric current to the active electrode drives the energy activatable material, such as the methylene blue, from the active electrode into the body. The other electrode, the return electrode, closes the electrical circuit to permit current flow through the active electrode and through the body.

Figure 8:
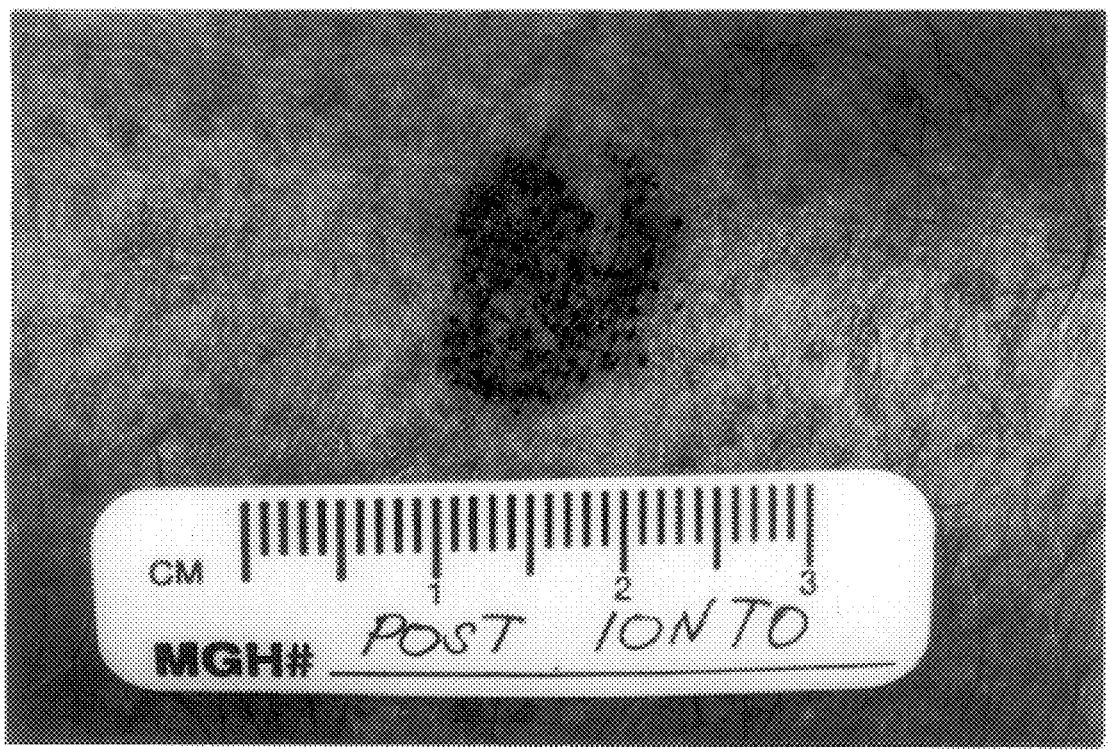
FIG. 8 depicts methylene blue which has been iontophoretically administered into the sebaceous glands and/or infundibulum of an individual.

In general, an energy activatable material is applied topically to the area to be treated as a solution or suspension. Typical solutions are aqueous based solutions, e.g., water, which can contain low molecular weight alcohols, e.g., ethanol, isopropanol, butanol. Penetration of the energy activatable material into the infundibulum and/or sebaceous gland is facilitated by iontophoretic application. Generally, the site of treatment and a major muscle site are cleansed with an alcoholic solution. A dispersive pad is applied over the major muscle at least 6 inches from the drug electrode site. A hydrated drug electrode pad is applied to the cleansed treatment site and appropriate lead clips are attached to the pads. Typically, the iontophoresis current is between about 0.1 to 40 mA/min, with a current of about 2 to 4 mA. The treatment period is generally between about 10 and 20 minutes and the treatment site can be from about 1 centimeter to about 11 centimeters in diameter. Those skilled in the art can identify those parameters necessary to administer the activatable material dependent upon the age, sex, weight, and skin condition of the individual. Energy activatable material concentrations are greatest in the infundibulum, ecrine ducts and sebaceous glands. Consequently, these structures are most affected by subsequent laser treatment. FIG. 8 depicts methylene blue which has been iontophoretically administered into the sebaceous glands and/or infundibulum of an individual.

As used herein, the term "iontophoresis device" refers generally to an electrically assisted device or apparatus suitable for the transdermal iontophoretic delivery of therapeutic levels of an energy activatable material to a mammal. Such iontophoresis devices are well known in the art and are also referred to as "iontophoretic delivery devices" or "electrotransport devices."

Iontophoresis devices and methods for using these devices in conjunction with the present invention are described, for example, in the following U.S. patent documents, the disclosures of which are incorporated herein by reference: U.S. Pat. Nos. 3,991,755; 4,141,359; 4,250,878; 4,395,545; 4,744,787; 4,747,819; 4,927,408; 5,080,646; 5,084,006; 5,125,894; 5,135,477; 5,135,480; 5,147,296; 5,147,297; 5,158,537; 5,162,042; 5,162,043; 5,167,616; 5,169,382; 5,169,383; 5,415,628; 5,203,768; 5,207,752; 5,221,254; 5,232,438; 5,234,992; 5,240,995; 5,246,417; 5,288,389; 5,298,017; 5,310,404; 5,312,326; 5,314,502; 5,320,598; 5,322,502; 5,326,341; 5,344,394; 5,374,242; 5,380,271; 5,385,543; 5,387,189; 5,395,310; 5,403,275; 5,405,317; 5,415,628; 5,423,739; 5,443,442; 5,445,606; 5,445,609; 5,464,387; 5,466,217; 4,950,229; 5,246,418; 5,256,137; 5,284,471; 5,302,172; 5,306,235; 5,310,403; 5,320,597; 5,458,569; 5,498,235; 4,557,723; 4,713,050; 4,865,582; 4,752,285; 5,087,242; 5,236,412; 5,281,287.

Either photothermal (i.e. using principles of selective photothermolysis) or photochemical (i.e., using principles of photodynamic therapy) mechanisms are utilized to affect the target structures, as a treatment to prevent sebaceous gland disorders, such as acne lesions, from forming. Methylene blue (MB) and many other light sensitive chromophores are potent photodynamic photosensitizers and can also be used as photothermal sensitizers. The red absorption maximum of methylene blue around 660 nm provides strong absorption for either mechanism. Another strong candidate dye is indocyanine green (ICG) (Cardiogreen®, Becton-Dickenson), which has very poor photodynamic activity but is an excellent photothermal chromophore. Indocyanine green is a zwitterion (neutral, highly polar molecule) which tends to bind strongly to proteins and is well suited for targeting the infundibulum by photothermal mechanisms. ICG absorbs maximally near 800 nm, a wavelength well suited for diode, Alexandrite lasers, and other light sources. For selective photothermolysis, pulses of intense red or near-infrared light in the ms time domain at the appropriate wavelength region should be delivered, for example using a pulsed dye laser, diode laser arrays, other pulsed or scanned lasers, or filtered flashlamp sources to deliver fluences in excess of 1 J/cm$^2$ per pulse. For photodynamic effects, lower average irradiance exposures given over longer exposure time would be appropriate for example approximately 10–100 mW/cm$^2$ delivered for about 100–2000 seconds (total fluence, 1–200 J/cm$^2$). For photodynamic effect, light sources such as light-emitting diodes, incandescent lamps, xenon arc lamps, lasers or sunlight can be used.

In order to form and retain a plug within the infundibulum, there must be a constriction along the outflow tract. As material including sebum, cells, or bacteria accumulate and are concentrated onto the plug, walls of the infundibulum are dilated until the middle or lower part of the infundibulum is larger in diameter than its outlet (the surface pore). If the outlet diameter can be increased, the plug is more likely to be expelled and pressure within the sebaceous follicle decreased before rupture can occur. The upper region of the infundibulum is also the source of follicular neck cells which shed into the infundibulum and add to the plug. For these reasons, the walls of the upper portion of the infundibulum and especially its pore at the skin surface are the primary target for energy activatable material-assisted sebaceous gland disorder treatment, e.g. acne treatment. In a manner conceptually similar to laser skin "resurfacing", the shape and size of the infundibulum and its outlet pore can be affected by energy activatable material-assisted photothermal or photochemical treatment. The dermis immediately surrounding sebaceous follicles, is largely responsible for maintaining shape of the infundibulum, and should be altered to produce a permanent affect. By using pulses in the ms time domain, there is time for thermal conduction from energy activatable material in the infundibulum, to the wall and immediately-surrounding dermal collagen of the infundibulum. Photothermal mechanisms are preferred because permanent changes are known to be induced in the dermis.

The invention is further illustrated by the following examples which in no way should be construed as being further limiting. The contents of all references, pending patent applications and published patent applications, cited throughout this application, including those referenced in the background section, are hereby incorporated by reference. It should be understood that the models used throughout the examples are accepted models and that the demonstration of efficacy in these models is predictive of efficacy in humans.

EXEMPLIFICATION

Fresh, in-vitro human sebaceous skin samples were used. Dye solutions and particle suspensions were applied to the samples at different concentration and in various vehicles, followed by localization of the dye by frozen sectioning and light microscopy. A number of FDA-approved laser sensitive dyes were examined and found that methylene blue and several others rapidly enter the infundibulum. Methylene blue proceeded to deeply and selectively stain the sebaceous glands, requiring several hours to do so. Apparently, almost any dye or suspension can be delivered to the upper infundibulum by direct solvent flow into the pore. Optimization of the concentration and solvent for MB and ICG can be determined by one skilled in the art. The effect of iontophoresis of MB in vitro should increase rate of uptake by at least one order of magnitude. Physical means of increasing dye uptake into the infundibulum, including ultrasonication with a tissue dismembranator at low intensity, and a simple pressure-applicator intended to open the surface pores while providing a pressure gradient in favor of dye uptake is possible.

For MB dye, a 660 nm source is required, preferably a pulsed dye laser operating with at least 1 ms pulse duration. There is essentially no absorption by MB at wavelengths longer than 690 nm, such that ruby and Alexandrite lasers are not useful. Similar in-vitro laser targeting can be performed using ICG in the infundibulum, and C-particle suspension (medical grade India Ink) to indicate that physical means deliver sufficient chromophore into the infundibulum.

EXPERIMENTALS

Experiment Using Methylene Blue to Stain Sebaceous Glands in ex vivo Tissue

Freshly excised human skin from a face-lift procedure was provided by a plastic surgeon. The skin originated from the periauricular area and the anterior hairline of a middle-aged fair-skinned female. The samples were stored at 4° C. overnight. On the day of experiment, the tissue was shaved with a razor and defatted by rubbing the surface with alcohol swabs for 1 minute. After cutting the skin in smaller pieces, the tissue was placed on saline-soaked gauzes. Methylene blue, a cationic hydrophilic dye was dissolved in distilled water, alcohol, and propylene glycol at a concentration of 5% and applied on the surface of the skin in a thick layer at 31° C. After 1 hour, the excess dye was removed with a dry absorbing gauze revealing a lightly stained epidermis with accentuation of the staining in the follicular pores in all specimen. 5 mm-punch biopsies were performed and the samples were processed frozen sections.

Figure 9:
FIG. 9 depicts light microscopy of blue staining of the epidermis, sebaceous glands and hair follicles.

Light microscopy of histologic sections showed dense blue staining of the epidermis and of some sebaceous glands and entire hair follicles (FIG. 9). There was minimal non-specific staining of the interstitial dermis.

Freshly excised human skin from a face-lift procedure was provided by a plastic surgeon. The skin originated from the periauricular area and the anterior hairline of a middle-aged fair-skinned female. The samples were stored at 4° C. overnight. On the day of experiment, the tissue was shaved with a razor and defatted by rubbing the surface with alcohol swabs for 1 minute. After cutting the skin in smaller pieces, the tissue was placed on saline-soaked gauzes. Methylene blue, a cationic hydrophilic dye was dissolved in distilled water, alcohol, and propylene glycol at a concentration of 5% and was mixed in a commercially available aqueous-based lotion (50 $\mu$L of dissolved dye in 500 mg of lotion) and applied on the surface of the skin in a thick layer at 31° C. After 1 hour, the excess dye was removed with a dry absorbing gauze revealing a lightly stained epidermis with accentuation of the staining in the follicular pores in all specimen. 5 mm-punch biopsies were performed and the samples were processed frozen sections.

Figure 10:
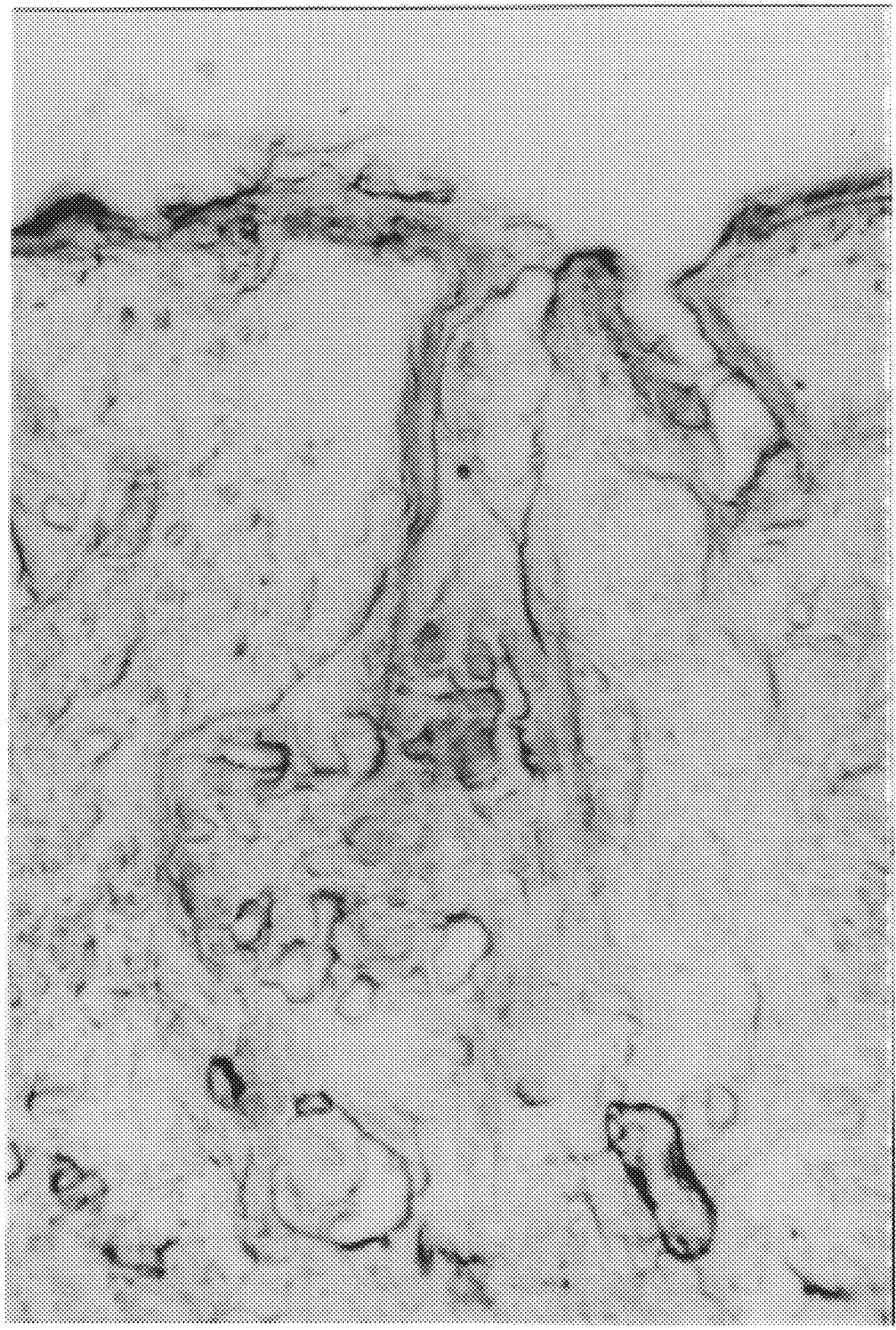
FIG. 10 is a color photograph depicts light microscopy of blue staining of the epidermis, sebaceous glands and hair follicles.

Light microscopy of histologic sections showed dense blue staining of the epidermis and of some sebaceous glands and entire hair follicles (FIG. 10). There was minimal non-specific staining of the interstitial dermis.

Methylene blue dye was also administered into the sebaceous glands via Retina Gel® (Ortho Pharmaceuticals) as the carrier vehicle. Typically, a sufficient amount of methylene blue (50 $\mu$L of dissolved dye in 500 mg of gel) was combined with hydroxypropyl cellulose, butylated hydroxytoluene and alcohol and applied to the epidermis. Penetration of the methylene blue dye into the sebaceous glands of freshly excised human skin was noted via light microscopy as described above.

EQUIVALENTS

Those skilled in the art will recognize, or be able to ascertain, using no more than routine experimentation, many equivalents to specific embodiments of the invention described specifically herein. Such equivalents are intended to be encompassed in the scope of the following claims.

What is claimed is:

1. A method for treating a sebaceous gland comprising the steps of
   a) topically applying an energy activatable material to a section of skin afflicted with a sebaceous gland disorder, the energy activated material comprising a chromophore containing group, wherein said material is activated by energy which penetrates outer layers of epidermis,
   b) iontophoretically causing a sufficient amount of said material to infiltrate into spaces in said skin; and c) exposing said section of skin to energy sufficient to cause said material to become photochemically or photothermally activated such that the activated material interacts with localized surrounding tissue, without photomechanical destruction of surrounding tissue, thereby treating said sebaceous gland disorder.

2. The method of claim 1, wherein said chromophore containing group is methylene blue.

3. The method of claim 1, wherein said chromophore containing group is a laser sensitive material.

4. The method of claim 3, wherein said laser sensitive material is methylene blue.

5. The method of claim 1, wherein said energy activatable material is suspended in a pharmaceutical carrier.

6. A method for modifying the opening to the infundibulum comprising the steps of:
   a) topically applying an energy activatable material to the opening to the infundibulum, the energy activatable material comprising a chromophore containing group, wherein said material is activated by energy which penetrates outer layers of epidermis,
   b) iontophoretically causing a sufficient amount of said material to infiltrate into spaces about said infundibulum; and
   c) exposing said section of skin with sufficient energy to cause said material to become photochemically or photothermally activated such that the activated material interacts with localized surrounding tissue, without photomechanical destruction of surrounding tissue, thereby modifying said opening to the infundibulum.

7. A method for modifying the pilosebaceous unit comprising the steps of:
   a) topically applying an energy activatable material to the pilosebaceous unit, the energy activatable material comprising a chromophore containing group, wherein said material is activated by energy which penetrates outer layers of epidermis,
   b) iontophoretically causing a sufficient amount of said material to infiltrate the pilosebaceous unit; and
   c) exposing said section of skin with sufficient energy to cause said material to become photochemically or photothermally activated such that the activated material interacts with localized surrounding tissue, without photomechanical destruction of surrounding tissue, thereby modifying the pilosebaceous unit.

* * * * *

UNITED STATES PATENT AND TRADEMARK OFFICE
CERTIFICATE OF CORRECTION

| | | |
|---|---|---|
| PATENT NO. | : 6,600,951 B1 | |
| APPLICATION NO. | : 09/464137 | |
| DATED | : July 29, 2003 | |
| INVENTOR(S) | : Richard R. Anderson | |

It is certified that error appears in the above-identified patent and that said Letters Patent is hereby corrected as shown below:

At column 1, line 5, before "BACKGROUND OF THE INVENTION", insert the following:

--STATEMENT REGARDING FEDERALLY SPONSORED RESEARCH

This invention was made with Government support under Grant No. N00014-94-1-0927 awarded by the U.S. Department of the Navy. The U.S. Government has certain rights in this invention.--

Signed and Sealed this

Seventh Day of July, 2009

JOHN DOLL
*Acting Director of the United States Patent and Trademark Office*